US007723511B2

(12) United States Patent
Cole et al.

(10) Patent No.: US 7,723,511 B2
(45) Date of Patent: *May 25, 2010

(54) SYNTHESIS OF SULFURIZED OLIGONUCLEOTIDES

(75) Inventors: Douglas L. Cole, Half Moon Bay, CA (US); Vasulinga Ravikumar, Carlsbad, CA (US); Zacharia S. Cheruvallath, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/106,889

(22) Filed: Apr. 21, 2008

(65) Prior Publication Data

US 2008/0293929 A1   Nov. 27, 2008

Related U.S. Application Data

(63) Continuation of application No. 10/847,502, filed on May 17, 2004, now Pat. No. 7,378,516, which is a continuation of application No. 10/181,200, filed as application No. PCT/US01/00715 on Jan. 10, 2001, now Pat. No. 7,227,015, which is a continuation of application No. 09/481,486, filed on Jan. 11, 2000, now Pat. No. 6,242,591.

(51) Int. Cl.
C07H 21/00 (2006.01)
C07C 321/00 (2006.01)
C07C 323/00 (2006.01)
C07C 381/00 (2006.01)

(52) U.S. Cl. ............... 536/25.3; 536/25.33; 536/25.34; 568/22

(58) Field of Classification Search ............... None
See application file for complete search history.

(56) References Cited

U.S. PATENT DOCUMENTS

| 3,923,763 | A | * | 12/1975 | Edmondson | 526/217 |
|---|---|---|---|---|---|
| 5,264,566 | A | * | 11/1993 | Froehler et al. | 536/25.34 |
| 5,902,881 | A | * | 5/1999 | Cheruvallath et al. | 536/25.3 |
| 6,114,519 | A | * | 9/2000 | Cole et al. | 536/25.34 |
| 6,242,591 | B1 | * | 6/2001 | Cole et al. | 536/25.3 |
| 7,227,015 | B2 | * | 6/2007 | Cole et al. | 536/25.3 |
| 7,378,516 | B2 | * | 5/2008 | Cole et al. | 536/25.34 |
| 2003/0212267 | A1 | * | 11/2003 | Cole et al. | 536/25.34 |

FOREIGN PATENT DOCUMENTS

| NL | 8902521 | | 10/1989 |
|---|---|---|---|
| WO | WO91/16331 | A1 * | 10/1991 |
| WO | WO 93/13118 | | 7/1993 |
| WO | WO 96/06853 | | 3/1996 |
| WO | WO96/09406 | A1 * | 3/1996 |
| WO | WO 99/19340 | | 4/1999 |
| WO | WO01/51502 | A1 * | 7/2001 |

OTHER PUBLICATIONS (V) Barany et al., "A General Strategy for Elaboration of the Dithiocarbonyl Functionality, -(C=O)SS-: Application to the Synthesis of Bis(chlorocarbonyl)disulfane and Related Derivatives of Thiocarbonic Acids," Journal of Organic Chemistry, 48(24), 4750-4761 (Dec. 2, 1983).*
(W) Carey et al., Advanced Organic Chemistry, 3rd Ed., Part A: Structure and Mechanisms, Plenum Press, New York, NY, 1990, only pp. 473-475 supplied.*
(R) Zhang et al.(I), "Synthesis and Properties of Novel Thiono Triester Modified Antisense Oligodeoxynucleotide Phosphorothioates," Bioorganic & Medicinal Chem. Letters, 5(15), 1735-1740 (Aug. 3, 1995).*
(S) Zhang et al. (II), "Thiono Triester Modified Antisense Oligonucleotides for Inhibition of Human Cytomegalovirus In Vitro," Bioorganic & Medicinal Chem. Letters, 6(16), 1911-1916 (Aug. 20, 1996).*
(T) Bokarev et al., "Synthesis of Bis(Alkyl Xanthyl) Trisulfides," Izv. Akad. Nauk SSSR, Ser. Khim., 1964(12), 2175-2182; Chemical Abstracts, 62(7), Abstr. No. 7631d (Mar. 29, 1965); only Abstract supplied.*
(U) Scholl et al., "Novel Symmetrical and Mixed Carbamoyl and Amino Polysulfanes by Reactions of (Alkoxydichloromethyl)polysulfuranyl Substrates with N-Methylaniline," Journal of Organic Chemistry, 51(10), 1866-1881 (1986).*
(X) Iyer et al.. "Solid-Phase Stereoselective Synthesis of Oligonucleotide Phosphorothioates: The Nucleoside Bicyclic Oxazaphospholidines as Novel Synthons," Tetrahedron Letters, 39, 2491-2494 (1998).*
Cheruvallath et al., "Sulfurization Efficiency in the Solution Phase Synthesis of Deoxyribonucleotide Phosphorothioates—Comparison of Sulfur Triethylamine with Various Sulfurizing Agents" Nucleosides Nucleotides (1996) 15:1441-1445.
Debont et al., "Solid-phase synthesis of O-phosphorothioylserine- and -theonine-containing peptides as well as O-phosphoserine- and -threonine-containing peptides" J. Org. Chem. (1993) 58(6) 1309-1317.
Dreef et al., "An expeditious synthesis of biologically important myo-inositol phosphorothioates" Bioorg. Med. Chem. Lett. (1991) 1(5): 239-242.
Eckstein et al., "Oligonucleotides and Analogues, a Practical Approach" Oxford University Press, New York, 1991.

(Continued)

*Primary Examiner*—Lawrence E Crane
(74) *Attorney, Agent, or Firm*—ISIS Patent Department

(57) ABSTRACT

Methods for the formation of sulfurized oligonucleotides are provided. The methods allow for the formation of phosphorothioate linkages in the oligonucleotides or derivatives, without the need for complex solvent mixtures and repeated washing or solvent changes. Oligonucleotides having from about 8, and up to about 50, nucleotides can be sulfurized according to the methods of the invention with higher yields than have been previously reported.

13 Claims, No Drawings

OTHER PUBLICATIONS

European Search Report for Serial No. EP 01901916.5 dated Feb. 21, 2003 (ISIS-4688).

International Search Reports for Serial No. PCT/US98/21502 dated Jan. 26, 1999 (ISIS-3141).

Iyer et al., "3H-1,2-benzodithiole-3-one 1,1-dioxide as an improved sulfurizing reagent in the solid-phase synthesis of oligodeoxyribonucleoside phosphorothioates" J. Am. Chem. (1990) 112:1253-1255.

Iyer et al., "The Automated Synthesis of Sulfur-Containing Oligodeoxyribonucleotides Using 3H-1,2-Benzodithiol-3-one 1,1-Dioxide as a Sulfur-Transfer Reagent" J. Org. Chem. (1990) 55(15):4693-4699.

Kamer et al., "An Efficient Approach Toward the Synthesis of Phosphorothioate Diesters Via the Schonberg Reaction" Tetra. Lett. (1989) 30(48):6757-6760.

Kodomari et al., "A Convenient Synthesis of Bis(acyl) Disulfides using Phase-Transfer Catalysis" Synthesis (1981) 637-638.

Kozikowski et al., "Tools for Cell Signaling: Synthesis of the 3-Phosphatase-Resistant 1,3,4,5-InsP4 Mimic, 1D-myo-Inositol 1,4,5-Trisphosphate 3-Phosphorothioate" J. Org. Chem. (1994) 59(9):2279-2281.

Lozano et al., "Electrosynthesis of 2-benzhydrylidene-4,4-diphenyl-1,3-oxathiolan-5-one: the reaction pathway" Tetrahedron (1996) 52(4):1259-1266.

Roelen et al., "A study on the use of phenylacetyl disulfide in the solid-phase synthesis of oligodeoxynucleoside phosphorothioates" Rech. Trav. Chim. Pays-Bas (1991) 110:325-331.

Wyrzykiewicz et al., "Efficiency of sulfurization in the synthesis of oligodeoxyribonucleotide phosphorothioates utilizing various sulfurizing reagents" Bioorg. Med. Chem. Lett. (1994) 4(12):1519-1522.

"Instrument Specific Safety" Models 392 and 394 User's Safety Summary (1994) Applied Biosystems, Inc. p. 2-10.

"Synthesizing Mixed Phosphorothioate and Phosphodiester Oligonucleotides" User Bulletin 65 (1991) Applied Biosystems, Inc. pp. UB65-UB65-12.

Cheruvallath et al., "Synthesis of Antisense Oligonucleotides: Replacement of 3H,1,2-Benzodithiol-3-one 1,1-Diozide (Beacuage Reagent) with Phenylacetyl Disulfide (PADS) As Efficient Sulfurization Reagent: From Bench to Bulk Manufacture of Active Pharmaceutical Ingredient" Organic Process Research & Development (2000) 4(3):199-204.

Hecker, "Auswahl von Losungsmittelsystemen zur multiplikativen Verteilung" Chimia (1954) 8:229-236.

EP Suppl. European Search Report for Application No. EP98953408.6 dated Apr. 2, 2001.

PCT International Search Report for Serial No. PCT/US01/00715 dated May 16, 2001.

* cited by examiner

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(20)
<223> OTHER INFORMATION: phosphorothioate 20-mer

<400> SEQUENCE: 1
tcccgcctgt gacatgcatt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(20)
<223> OTHER INFORMATION: phosphorothioate 20-mer

<400> SEQUENCE: 2
gcccaagctg gcatccgtca                                              20

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(21)
<223> OTHER INFORMATION: phosphorothioate 21-mer

<400> SEQUENCE: 3
gcgtttgctc ttcttcttgc g                                            21

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct
<220> FEATURE:

```
<221> NAME/KEY: misc_feature
<222> LOCATION: (1)...(20)
<223> OTHER INFORMATION: phosphorothioate 20-mer

<400> SEQUENCE: 4
gttctcgctg gtgagtttca                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)...(13)
<223> OTHER INFORMATION: 2'-methoxyethyl
<220> FEATURE:
<221> NAME/KEY: misc_feature
<222> LOCATION: (1)...(20)
<223> OTHER INFORMATION: phosphorothioate 20-mer

<400> SEQUENCE: 5
tcccgcctgt gacaugcauu                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)...(13)
<223> OTHER INFORMATION: 2'-methoxyethyl
<220> FEATURE:
<221> NAME/KEY: misc_feature
<222> LOCATION: (1)...(20)
<223> OTHER INFORMATION: phosphorothioate 20-mer

<400> SEQUENCE: 6
tcccgcctgt gacaugcauu                                              20

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: 2'-methoxyethyl
<220> FEATURE:
<221> NAME/KEY: misc_feature
<222> LOCATION: (15)...(15)
<223> OTHER INFORMATION: 2'-methoxyethyl
<220> FEATURE:
<221> NAME/KEY: misc_feature
<222> LOCATION: (1)...(21)
<223> OTHER INFORMATION: phosphorothioate 21-mer

<400> SEQUENCE: 7
gcguuugctc ttctucuugc g                                            21

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct
```

```
<220> FEATURE:
<221> NAME/KEY: misc_feature
<222> LOCATION: (12)...(13)
<223> OTHER INFORMATION: 2'-methoxyethyl
<220> FEATURE:
<221> NAME/KEY: misc_feature
<222> LOCATION: (1)...(20)
<223> OTHER INFORMATION: phosphorothioate 20-mer

<400> SEQUENCE: 8
gcccaagctg gcauccguca                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)...(13)
<223> OTHER INFORMATION: 2'-methoxyethyl
<220> FEATURE:
<221> NAME/KEY: misc_feature
<222> LOCATION: (1)...(20)
<223> OTHER INFORMATION: phosphorothioate 20-mer

<400> SEQUENCE: 9
gcccaagctg gcauccguca                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: 2'-O-methoyxethyl
<220> FEATURE:
<221> NAME/KEY: misc_feature
<222> LOCATION: (1)...(20)
<223> OTHER INFORMATION: phosphorothioate 20-mer

<400> SEQUENCE: 10
tttttttttt tttttttttt                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: 2'-O-methoxyethyl
<220> FEATURE:
<221> NAME/KEY: misc_feature
<222> LOCATION: (16)...(16)
<223> OTHER INFORMATION: 2'-O-methoxyethyl
<220> FEATURE:
<221> NAME/KEY: misc_feature
<222> LOCATION: (1)...(20)
<223> OTHER INFORMATION: phosphorothioate 20-mer

<400> SEQUENCE: 11
gctgattaga gagaggtccc                                               20

<210> SEQ ID NO 12
```

```
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: 2'-O-methoxyethyl
<220> FEATURE:
<221> NAME/KEY: misc_feature
<222> LOCATION: (13)...(13)
<223> OTHER INFORMATION: 2'-O-methoxyethyl
<220> FEATURE:
<221> NAME/KEY: misc_feature
<222> LOCATION: (1)...(20)
<223> OTHER INFORMATION: phosphorothioate 20-mer

<400> SEQUENCE: 12
ctgagtctgt tttccattct                                           20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)...(13)
<223> OTHER INFORMATION: 2'-O-methoxyethyl
<220> FEATURE:
<221> NAME/KEY: misc_feature
<222> LOCATION: (1)...(20)
<223> OTHER INFORMATION: phosphorothioate 20-mer

<400> SEQUENCE: 13
tcccgcctgt gacatgcatt                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)...(13)
<223> OTHER INFORMATION: 2'-O'methoxyethyl
<220> FEATURE:
<221> NAME/KEY: misc_feature
<222> LOCATION: (1)...(20)
<223> OTHER INFORMATION: phosphorothioate 20-mer

<400> SEQUENCE: 14
gcccaagctg gcatccgtca                                           20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: 2'-O-methyl
<220> FEATURE:
<221> NAME/KEY: misc_feature
<222> LOCATION: (1)...(20)
<223> OTHER INFORMATION: phosphorothioate 20-mer

<400> SEQUENCE: 15
```

```
tttttttttt tttttttttt                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: 2'-O-methyl
<220> FEATURE:
<221> NAME/KEY: misc_feature
<222> LOCATION: (15)...(16)
<223> OTHER INFORMATION: 2'-O-methyl
<220> FEATURE:
<221> NAME/KEY: misc_feature
<222> LOCATION: (1)...(20)
<223> OTHER INFORMATION: phosphorothioate 20-mer

<400> SEQUENCE: 16
gctgattaga gagaggtccc                                              20
```

SYNTHESIS OF SULFURIZED OLIGONUCLEOTIDES

CROSS REFERENCE TO RELATED APPLICATION

This application is a continuation of U.S. application Ser. No. 10/847,502, filed on May 17, 2004, now U.S. Pat. No. 7,378,516; which is a continuation of U.S. application Ser. No. 10/181,200, filed on Dec. 12, 2002, now U.S. Pat. No. 7,227,015; which is the U.S. National Stage of International Application No. PCT/US01/00715, filed Jan. 10, 2001 and published as WO01/51502; which is a continuation of U.S. application Ser. No. 09/481,486, filed Jan. 11, 2000, and now U.S. Pat. No. 6,242,591, all of which are hereby incorporated by reference in their entirety.

SEQUENCE LISTING

The present application is being filed along with a Sequence Listing in electronic format. The Sequence Listing is provided as a file entitled ISIS5479USC1SEQ.txt, created on Apr. 21, 2008, which is 2.47 Kb in size. The information in the electronic format of the sequence listing is incorporated herein by reference in its entirety.

FIELD OF THE INVENTION

The present invention is directed to methods for synthesizing sulfurized oligonucleotides and analogs thereof. The methods employ a phenylacetyl disulfide reagent in a simplified solvent system and produce oligonucleotides having phosphorothioate groups with great efficiency and improved yields.

BACKGROUND OF THE INVENTION

Modified oligonucleotides are of great value in molecular biological research and in applications such as anti-viral therapy. Modified oligonucleotides which can block RNA translation, and are nuclease resistant, are useful as antisense reagents. Sulfurized oligonucleotides, which contain phosphorothioate (P—S) linkages, are of interest in these areas. Phosphorothioate-containing oligonucleotides are also useful in determining the stereochemical pathways of certain enzymes which recognize nucleic acids.

Standard techniques for sulfurization of phosphorous-containing compounds have been applied to the synthesis of sulfurized oligonucleotides. Examples of sulfurization reagents which have been used to synthesize oligonucleotides containing phosphorothioate bonds include elemental sulfur, dibenzoyl tetrasulfide, 3-H-1,2-benzidithiol-3-one 1,1-dioxide (also known as Beaucage reagent), tetraethylthiuram disulfide (TETD), and bis(O,O-diisopropoxy phosphinothioyl) disulfide (known as Stec reagent). Most of the known sulfurization reagents, however, have one or more significant disadvantages.

Elemental sulfur presents problems and is not suitable for automation because of its insolubility in most organic solvents. Furthermore, carbon disulfide, a preferred source of sulfur, has undesirable volatility and an undesirably low flash point. Unwanted side products are often observed with the use of dibenzoyl tetrasulfide. Beaucage reagent, while a relatively efficient sulfurization reagent, is difficult to synthesize and not particularly stable. Furthermore, use of Beaucage reagent forms a secondary reaction product which is a potent oxidizing agent. (R. P. Iyer et al., *J. Am. Chem. Soc.* 112, pp. 1253-1254 (1990); R. P. Iyer et al., *J. Org. Chem.* 55, 4693-4699 (1990)). This can further lead to unwanted side products which can be difficult to separate from the desired reaction product. Tetraethylthiuram disulfide, while relatively inexpensive and stable, has a sulfurization reaction rate which can be undesirable slow.

A method for producing a phosphorothioate ester by reaction of a phosphite ester with an acyl disulfide is disclosed in Dutch patent application No. 8902521. The disclosed method is applied to a purified phosphotriester dimer utilizing solution phase chemistry. The method is time and labor intensive in that it was only shown to work in a complex scheme which involved carrying out the first stage of synthesis (formation of a phosphite) in acetonitrile, removing the acetonitrile, purifying the intermediate phosphotriester, and proceeding with the sulfurization in a solvent mixture of dichloroethane (DCE) and 2,4,6-collidine. Furthermore, the method was demonstrated only with a dinucleotide. There was no suggestion that the Dutch method could be employed with larger nucleic acid structures, that the same could employ a common solvent throughout all steps of synthesis, that improved yields could be obtained, or that the method could be adapted for conventional automated synthesis without extensive modification of the scheme of automation. Although acetonitrile is mentioned as one of several possible solvents, utility of the method for carrying out all steps of the synthesis in acetonitrile as a common solvent was not demonstrated. While other publications (Kamer et al., Tetrahedron Letters 30(48), pp. 6757-6760 (1989); Roelen et al., Rech. Trav. Chim. Pays-Bas 110, pp. 325-331 (1991)) show sulfurization of oligomers having up to 6 nucleotides, the foregoing shortcomings are not overcome by the methods disclosed in these references.

Thus, there remains a need for improved methods and reagents for preparing sulfur-containing phosphorous groups, such as phosphorothioate linkages, in oligonucleotides and other organic compounds. The present invention is directed to these, as well as other, important ends.

SUMMARY OF THE INVENTION

The present invention provides methods for synthesis of phosphorothioate oligonucleotides with improved yields as compared to those obtained with prior methods. Moreover, the present methods are useful for the synthesis of not only phosphorothioate oligonucleotides having relatively large numbers of nucleotide and/or nucleoside units therein, e.g. from about 6 to about 50, and even more, and particularly from about 8 to about 30 nucleotide and/or nucleoside units. The methods of the present invention employ a greatly simplified solvent system, one which is compatible with automated synthetic reaction schemes and commercial synthesizers. The resulting improvement in synthetic opportunities permits wide application of the present methods throughout nucleic acid chemistry.

One aspect of the present invention discloses methods for synthesizing phosphorothioate oligonucleotides, comprising the steps of phosphitylating a 5'-hydroxyl moiety of a nucleotide, nucleoside, oligonucleotide or an oligonucleoside, and contacting the resultant phosphite intermediate with a phenylacetyl disulfide in the presence of a solvent system that includes acetonitrile for a time sufficient to effect the formation of a phosphorothioate functional group. Phosphorothioate oligonucleotides having a predetermined length and sequence can be prepared by repeating the phosphitylating and oxidizing steps.

In further aspects of the present invention, methods for the synthesis of phosphorothioate oligonucleotide analogs are disclosed, comprising the substitution of modified nucleotides, nucleosides, oligonucleotides and oligonucleosides for nucleotides, nucleosides, oligonucleotides or oligonucleosides. Modifications to nucleotides, nucleosides, oligonucleotides and oligonucleosides are well known in the art. As used herein the term "phosphorothioate oligonucleotide" is meant to include analogs as defined above.

The term "phosphite moiety" as used herein is meant to include phosphite moieties within nucleosides, nucleotides, oligonucleosides and oligonucleotides. In a preferred embodiment, phosphite moieties are in an activated state such as a dimethoxytritylphosphoramidite. The terms "nucleotide, nucleoside, oligonucleotide or an oligonucleoside" as used herein are intended to include both naturally occurring species and non-naturally occurring or modified species as is known to those skilled in the art. Common modifications include sugar modifications such as 2' modifications and base modifications or the use of substitute bases. When an oligonucleotide or modified oligonucleotide is used as the phosphite moiety, modified linkages as is commonly known in the art may also be present.

The present methods have demonstrated lower levels of impurities and higher yields compared to when DCE is used as a solvent for the oxidation step. The present methods have also shown, unexpectedly, that yields of about 99% can be obtained in acetonitrile/picoline. Acetonitrile/picoline is entirely compatible with automated synthesis without extensive modification to the synthetic routine, so that the present methods can be advantageously used in an automated synthesizer. For example, extensive washes are not required because a single solvent or mixture having a common solvent is used in all automated synthetic steps. Thus, solvent removal and wash steps can be eliminated. It has also been surprisingly discovered that high yields can be achieved when synthesizing phosphorothioate oligonucleotides or oligonucleotide analogs having from about 8 nucleotides and up to about 30 nucleotides.

Suitable solvent systems for use in the oxidation of the phosphite intermediate of the present invention include mixtures of two or more solvents. Preferably a mixture of an aprotic solvent with a protic or basic solvent. Preferred solvent mixtures include acetonitrile/picoline and acetonitrile/lutidine. Suitable aprotic solvents include pyridine and hindered pyridines such as lutidine, collidine, and picoline. Solvent mixtures can include, for example, two solvents such as acetonitrile and picoline, or acetonitrile and lutidine, in a volume ratio of from about 1:1.5 to about 1.5:1, preferably about 1:1.

Sulfurization (oxidation utilizing a sulfurizing reagent), according to the methods of the present invention, is carried out by contacting an oligonucleotide or analog with an acetyl disulfide for a time sufficient to effect formation of a phosphorothioate functional group. Preferred reagents include phenylacetyl disulfide, arylacetyl disulfide, and aryl substituted phenylacetyl disulfides.

Contacting the phosphite moiety with acetyl disulfide can be done using procedures and equipment known to those skilled in the art. For example, a glass reactor such as a flask can be suitably employed. Preferably, solid phase synthesis procedures are employed, and a solid support such as controlled pore glass. Even more preferably, the methods of the present invention can be carried out using automatic DNA synthesizers. Suitable solid phase techniques, including automated synthesis techniques, are described in F. Eckstein (ed.), *Oligonucleotides and Analogues, a Practical Approach*, Oxford University Press, New York (1991).

The methods of the present invention can be suitably carried out at room temperature. "Room temperature" includes ambient temperatures from about 20° C. to about 30° C. Reaction times are on the order of minutes, such as, for example, 2, 3, 4, or 5 minutes, or even as short as about 100 seconds.

Generally, methods of the present invention include phosphitylating the 5'-hydroxyl group of a nucleic acid moiety to form a phosphite intermediate and oxidizing the phosphite intermediate with an acetyl disulfide for a time sufficient to effect conversion of the phosphite intermediate to a phosphorothioate. The phosphite intermediate can be, for example, a phosphite linked dinucleotide, or an oligonucleotide or oligonucleoside having at least one phosphite linkage therein. The phosphitylation and oxidation steps of the method are both performed in a system that includes acetonitrile. Repetition of the phosphitylation and oxidation steps will give the phosphorothioate oligonucleotide having a predetermined length. Reaction progress can be monitored by well-known techniques such as proton or $^{31}$P NMR. The reaction product can be treated with a base such as, for example, ammonium hydroxide solution at a concentration of about 30 percent. The desired product can be readily isolated by, for example, standard filtration techniques.

The following examples are merely illustrative of the present invention and should not be considered limiting of the scope of the invention in any way. These examples and equivalents thereof will become more apparent to those skilled in the art in light of the present disclosure and the accompanying claims.

EXAMPLE 1

Synthesis of 5'-TTTTTTT'-3' Phosphorothioate Heptamer 50 milligram (2 μmole) of 5'-O-dimethoxytritylthymidine bound to CPG (controlled pore glass) through an ester linkage is taken up in a glass reactor, and a dichloromethane solution of 2% dichloroacetic acid (volume/volume) is added to deprotect the 5' hydroxyl group. The product is washed with acetonitrile. Then, a 0.2 M solution of 5'-O-(4,4'-dimethoxytrityl)thymidine-3'-O-(2-cyanoethyl N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile, and then a solution of acetic anhydride/lutidine/THF (1:1:8), and N-methyl imidazole/THF is added to cap any unreacted 5'-hydroxyl group. The product is washed with acetonitrile.

This complete cycle is repeated five more times to produce the completely protected thymidine heptamer. The carrier containing the compound is treated with 30% aqueous ammonium hydroxide solution for 90 minutes at room temperature. The aqueous solution is filtered, and concentrated under reduced pressure to give a phosphorothioate heptamer, TTTTTTT.

EXAMPLE 2

Synthesis of 5'-d(GACT)-3'Phosphorothioate Tetramer 50 milligram ($2\times10^{-6}$ mole (2 μmole)) of 5'-O-dimethoxytritylthymidine bound to CPG (controlled pore glass) through an ester linkage is taken up in a glass reactor, and a dichloromethane solution of 2% dichloroacetic acid (volume/volume) is added to deprotect the 5'-hydroxyl group. The product is washed with acetonitrile. Then, a 0.2 M solution of 5'-O-(4,4'-dimethoxytrityl)thymidine-3'-O-(2-cyanoethyl N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A solution of 2% dichloroacetic acid (volume/volume) is added to deprotect the 5'-hydroxyl group—The product is washed with acetonitrile. Then, a 0.2 M solution of $N^4$-benzoyl-5'-O-(4,4' dimethoxytrityl)-2'-deoxycytidine-3'-O-(2-cyanoethyl N,N'diisopropyl phosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3 picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap any unreacted 5'-hydroxyl group. The product is washed with acetonitrile.

A solution of 2% dichloroacetic acid (volume/volume) is added to deprotect the 5'-hydroxyl group. The product is washed with acetonitrile. Then, a 0.2 M solution of $N^6$-benzoyl-5'-O-(4,4'dimethoxytrityl)-2'-deoxyadenosine-3'-O-(2-cyanoethyl-N,N' diisopropylphosphoramidite) in anhydrous acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes—The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A solution of 2% dichloroacetic acid (volume/volume) is added to deprotect the 5'-hydroxyl group. The product is washed with acetonitrile. Then, a 0.2 M solution of $N^2$-isobutyryl-5'-O-4,4' dimethoxytrityl-deoxyguanosine-3'-O-(2-cyanoethyl N,N' diisopropyl phosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile: 3 picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap any unreacted 5'-hydroxyl group. The product is washed with acetonitrile.

The carrier containing the compound is treated with 30% aqueous ammonium hydroxide solution for 90 minutes at room temperature and then incubated at 55° C. for 24 hour. The aqueous solution is filtered, concentrated under reduced pressure to give a phosphorothioate tetramer of 5'-dG-dA-dC-T-3'.

EXAMPLE 3

Synthesis of fully-modified 5'-d(TCC-CGC-CTG-TGA-CAT-GCA-TT)-3' phosphorothioate 20-mer
<Seq. ID No. 1>

The synthesis of the above sequence was performed on a Pharmacia OligoPilot II Synthesizer on a 620 μmole scale using the cyanoethyl phosphoramidites and Pharmacia's primar support. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified as has been previously illustrated above.

EXAMPLE 4

Synthesis of fully-modified 5'd(GCC-CAA-GCT-GGC-ATC-CGT-CA)-3'phosphorothioate 20-mer
<Seq. ID No. 2>

The synthesis of the above sequence was performed on a Pharmacia OligoPilot II Synthesizer on a 620 μmole scale using the cyanoethyl phosphoramidites and Pharmacia's primar support. Sulfurization was performed using a 0.2 M solution of phenylacetyl disulfide in acetonitrile:3-picoline (1:1 v/v) for 2 minutes—At the end of synthesis, the support was washed with acetonitrile, cleaved, deprotected and purified as has been previously illustrated above.

EXAMPLE 5

Synthesis of fully-modified 5'-d(GCG-TTT-GCT-CTT-CTT-CTT-GCG)-3' phosphorothioate 21-mer
<Seq. ID No. 3>

The synthesis of the above sequence was performed on a Pharmacia OligoPilot II Synthesizer on a 620 μmole scale using the cyanoethyl phosphoramidites and Pharmacia's primar support. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified as has been previously illustrated above.

EXAMPLE 6

Synthesis of fully-modified 5'd(GTT-CTC-GCT-GGT-GAG-TTT-CA)-3' phosphorothioate 20-mer
<Seq. ID No. 4>

The synthesis of the above sequence was performed on a Pharmacia OligoPilot II Synthesizer on a 620 μmole scale using the cyanoethyl phosphoramidites and Pharmacia's primar support. Sulfurization was performed using a 0.2 M solution of phenylacetyl disulfide in acetonitrile:3-picoline (1:1 v/v) for 2 minutes. At the end of synthesis, the support

EXAMPLE 7

Synthesis of fully-modified 5'd(TCC-CGC-CTG-TGA)-2'-methoxyethyl-(CAU-GCA-UU)-3' phosphorothioate 20-mer <Seq. ID No. 5>

The synthesis of the above sequence was performed on a Milligen 8800 Synthesizer on a 282 μmole scale using the cyanoethyl phosphoramidites and Pharmacia's primar support. Sulfurization was performed using a 0.4 M solution of phenylacetyl disulfide in acetonitrile:3-picoline (1:1 v/v) for 6 minutes. At the end of synthesis, the support was washed with acetonitrile, cleaved, deprotected and purified as has been previously illustrated above.

EXAMPLE 8

Synthesis of fully-modified 5'd(TCC-CGC-CTG-TGA)2'methoxyethyl-(CAU-GCA-UU)-3' phosphorothioate 20-mer <Seq. ID No. 6>

The synthesis of the above sequence was performed on a Pharmacia OligoPilot II Synthesizer on a 250 μmole scale using the cyanoethyl phosphoramidites and Pharmacia's primar support. Sulfurization was performed using a 0.4 M solution of phenylacetyl disulfide in acetonitrile:3-picoline (1:1 v/v) for 10 minutes. At the end of synthesis, the support was washed with acetonitrile, cleaved, deprotected and purified as has been previously illustrated above.

EXAMPLE 9

Synthesis of fully-modified 5'-[2'-methoxyethyl (GCGUUUG)-d[CTCTTCT]-[2'-methoxyethyl-(UCUUGC)-dG-3' phosphorothioate 21-mer <Seq. ID No. 7>

The synthesis of the above sequence was performed on a Pharmacia OligoPilot II Synthesizer on a 250 μmole scale using the cyanoethyl phosphoramidites and Pharmacia's primar support. Sulfurization was performed using a 0.4 M solution of phenylacetyl disulfide in acetonitrile:3-picoline (1-1 v/v) for 6 minutes. At the end of synthesis, the support was washed with acetonitrile, cleaved, deprotected and purified as has been previously illustrated above.

EXAMPLE 10

Synthesis of fully-modified 5'-d(GCC-CAA-GCT-GGC)-2'-methoxyethyl-(AUC-CGU-CA)-3' phosphorothioate 20-mer <Seq. ID No. 8>

The synthesis of the above sequence was performed on a Milligen 8800 Synthesizer on a 565 μmole scale using the cyanoethyl phosphoramidites and Pharmacia's primar support. Sulfurization was performed using a 0.4 M solution of phenylacetyl disulfide in acetonitrile:3-picoline (1:1 v/v) for 6 minutes. At the end of synthesis, the support was washed with acetonitrile, cleaved, deprotected and purified as has been previously illustrated above.

EXAMPLE 11

Synthesis of fully-modified 5'-d(GCC-CAA-GCT-GGC)-2'-methoxyethyl-(AUC-CGU-CA)-3' phosphorothioate 20-mer <Seq. ID No. 9>

The synthesis of the above sequence was performed on a Pharmacia OligoPilot II Synthesizer on a 680 μmole scale using the cyanoethyl phosphoramidites and Pharmacia's primar support. Sulfurization was performed using a 0.4 M solution of phenylacetyl disulfide in acetonitrile:3-picoline (1:1 v/v) for 6 minutes. At the end of synthesis, the support was washed with acetonitrile, cleaved, deprotected and purified as has been previously illustrated above.

EXAMPLE 12

Synthesis of fully-modified 5'-[2'-O-methoxyethyl-(TTT-TTT-TTT-TTT-TTT-TTT-TT)-3' phosphorothioate 20-mer <Seq. ID No. 10>

The synthesis of the above homo-pyrimidine sequence was performed on a Pharmacia OligoPilot 11 synthesizer on an 180 μmole scale using cyanoethyl phosphoramidite of 5'-O-DMT-2'-O-methoxyethyl-5-methyluridine. Pharmacia's HL 30 primer support loaded with 2'-O-methoxyethyl-5-methyluridine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was treated with a solution of triethylamine: acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder. The stepwise sulfurization efficiency was found to 99.6% based on $^{31}$P NMR (D$_2$O).

EXAMPLE 13

Synthesis of fully-modified 5'-[2'-O-methoxyethyl-(TTT-TTT-TTT-TTT-TTT-TTT-TT)-3' phosphorothioate 20-mer <Seq. ID No. 10>

The synthesis of the above homo-pyrimidine sequence was performed on a Pharmacia OligoPilot II synthesizer on an 180 μmole scale using cyanoethyl phosphoramidite of 5'-O-DMT-2'-O-methoxyethyl-5-methyluridine. Pharmacia's HL 30 primer support loaded with 2'-O-methoxyethyl-5-methyluridine was used. Detritylation was performed using 3% dichloroacetic acid in toluene (volume/volume). Activation of phosphoramidite was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder. The stepwise sulfurization efficiency was found to 99.7% based on $^{31}$P NMR (D$_2$O).

EXAMPLE 14

Synthesis of fully-modified 5'-[2'-O-methoxyethyl-(GCTGA]-d(TTA-GAG-AGA-G)-[2'-O-methoxy-ethyl-(GTCCC)-3' phosphorothioate 20-mer <Seq. ID No. 11>

The synthesis of the above sequence was performed on a Pharmacia OligoPilot II synthesizer on an 180 μmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-N4-benzoyl-5-methylcytidine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylayed, precipitated and lyophilized to a powder. The stepwise sulfurization efficiency was found to 99.7% based on $^{31}$P NMR (D$_2$O).

EXAMPLE 15

Synthesis of fully-modified 5'-[2'-O-methoxyethyl-(CTG]-d(AGT-CTG-TTT)-[2'-O-methoxyethyl-(TCC-ATT-CT)-3' phosphorothioate 20-mer <Seq. ID No. 12>

The synthesis of the above sequence was performed on a Pharmacia OligoPilot II synthesizer on a 172 μmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-5-methyluridine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder. The stepwise sulfurization efficiency was found to 99.7% based on $^{31}$P NMR (D$_2$O).

EXAMPLE 16

Synthesis of fully-modified 5'-[2'-O-methoxyethyl-(GCTGA]-d(TTA-GAG-AGA-G)-[2'-O-methoxy-ethyl-(GTCCC)-3' phosphorothioate 20-mer <Seq. ID No. 11>

The synthesis of the above sequence was performed on a Pharmacia OligoProcess I Synthesizer on a 150 mmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-N4-benzoyl-5-methylcytidine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2.2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. The DMT-on peak was fractionated, analyzed by capillary gel electrophoresis, combined, detritylated, precipitated and lyophilized to a powder. The stepwise sulfurization efficiency was found to 99.75% based on $^{31}$P NMR (D$_2$O).

EXAMPLE 17

Synthesis of fully-modified 5'-[2'-O-methoxyethyl-(CTG]-d(AGT-CTG-TTT)-[2'-O-methoxyethyl-(TCC-ATT-CT)-3' phosphorothioate 20-mer <Seq. ID No. 12>

The synthesis of the above sequence was performed on a Pharmacia OligoPilot II synthesizer on a 40 mmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-5-methyluridine was used. Detritylation was performed using 15% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2.2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. The DMT-on peak was fractionated, analyzed by capillary gel electrophoresis, combined, detritylated, precipitated and lyophilized to a powder. The stepwise sulfurization efficiency was found to 99.7% based on $^{31}$P NMR (D$_2$O).

EXAMPLE 18

Synthesis of fully modified 5'-d(TCC-CGC-CTG-TGA)-2'-O-methoxyethyl-(CAT-GCA-TT)-3' phosphorothioate 20-mer <Seq. ID No. 13>

The synthesis of the above sequence was performed on a Milligen 8800 synthesizer on a 282 μmole scale using the cyanoethyl phosphoramidites and Pharmacia's HL 30 primer support. Detritylation was performed using 3% dichloroacetic acid in toluene (volume/volume). Sulfurization was performed using a 0.4 M solution of phenylacetyl disulfide in acetonitrile:3-picoline (1:1 v/v) for 4 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. The DMT-on peak was fractionated, analyzed by capillary gel electrophoresis, combined, detritylated, precipitated and lyophilized to a powder.

EXAMPLE 19

Synthesis of fully-modified 5'-[2'-O-methoxyethyl-(GCTGA]-d(TTA-GAG-AGA-G)-[2'-O-methoxy-ethyl-(GTCCC)-3' phosphorothioate 20-mer <Seq. ID No. 11>

The synthesis of the above sequence was performed on a Pharmacia OligoPilot II synthesizer on a 180 μmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-$N^4$-benzoyl-5-methylcytidine was used. Detritylation was performed using 3% dichloroacetic acid in toluene (volume/volume). Activation of phosphoramidite was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder.

EXAMPLE 20

Synthesis of fully modified 5'-[2'-methoxyethyl-(CTG)-d(AGT-CTG-TTT)-[2'-methoxyethyl-(TCC-ATT-CT)-3' phosphorothioate 20-mer <Seq. ID No. 12>

The synthesis of the above sequence was performed on a Pharmacia OligoPilot II synthesizer on a 172 μmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-5-methyluridine was used. Detritylation was performed using 3% dichloroacetic acid in toluene (volume/volume). Activation of phosphoramidite was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder.

EXAMPLE 21

Synthesis of fully modified 5'-d(GCC-CAA-GCT-GGC)-2'-O-methoxyethyl-(ATC-CGT-CA)-3' phosphorothioate 20-mer <Seq. ID No. 14>

The synthesis of the above sequence was performed on a Milligen 8800 synthesizer on a 282 μmole scale using the cyanoethyl phosphoramidites and Pharmacia's HL 30 primer support. Detritylation was performed using 3% dichloroacetic acid in toluene (volume/volume). Sulfurization was performed using a 0.4 M solution of phenylacetyl disulfide in acetonitrile:3-picoline (1:1 v/v) for 4 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. The DMT-on peak was fractionated, analyzed by capillary gel electrophoresis, combined, detritylated, precipitated and lyophilized to a powder.

EXAMPLE 22

Synthesis of fully-modified 5'-[2'-O-methyl-(TTT-TTT-TTT-TTT-TTT-TTT-TT)-3' phosphorothioate 20-mer <Seq. ID No. 15>

The synthesis of the above homo-pyrimidine sequence was performed on a Pharmacia OligoPilot II synthesizer on a 180 μmole scale using cyanoethyl phosphoramidite of 5'-O-DMT-2'-O-methyl-5-methyluridine. Pharmacia's HL 30 primer support loaded with 2'-O-methyl-5-methyluridine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder.

EXAMPLE 23

Synthesis of fully-modified 5'-[2'-O-methyl-(TTT-TTT-TTT-TTT-TTT-TTT-TT)-3' phosphorothioate 20-mer <Seq. ID No. 15>

The synthesis of the above homo-pyrimidine sequence was performed on a Pharmacia OligoPilot II synthesizer on a 180 μmole scale using cyanoethyl phosphoramidite of 5'-O-DMT-2'-O-methyl-5-methyluridine. Pharmacia's HL 30 primer support loaded with 2'-O-methyl-5-methyluridine was used. Detritylation was performed using 3% dichloroacetic acid in toluene (volume/volume). Activation of phosphoramidite was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder.

EXAMPLE 24

Synthesis of fully-modified 5'-[2'-O-methyl-(GCTGA]-d(TTA-GAG-AGA-G)-[2'-O-methyl-(GTCCC)-3' phosphorothioate 20-mer <Seq. ID No. 16>

The synthesis of the above sequence was performed on a Pharmacia OligoPilot II synthesizer on a 180 μmole scale using cyanoethyl phosphoramidite of 2'-deoxyribonucleosides and 2'-O-methyl substituted ribonucleosides. Pharmacia's HL 30 primer support loaded with 2'-O-methyl-N4-benzoyl-5-methylcytidine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder. The stepwise sulfurization efficiency was found to 99.5% based on $^{31}$P NMR ($D_2O$).

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

Various modifications of the invention, in addition to those described herein, will be apparent to those skilled in the art from the foregoing description. Such modifications are intended to fall within the scope of the appended claims.

What is claimed is:

1. A method for the preparation of a phosphorothioate internucleoside linkage comprising:

contacting the 5' hydroxyl group of a solid support bound nucleic acid moiety with a phosphite moiety in acetonitrile to form a phosphite diester intermediate; said phosphite moiety being bonded to a nucleoside, a nucleotide, an oligonucleoside or an oligonucleotide; and oxidizing said phosphite diester intermediate with an arylacetyl disulfide in a solvent mixture of acetonitrile and a lutidine, acetonitrile and a collidine and/or acetonitrile and a picoline in a ratio of 1.5:1 to 1:1.5, for a time sufficient to effect conversion of said phosphite diester intermediate to said phosphorothioate.

2. The method of claim 1 wherein said solvent mixture is either acetonitrile and a lutidine or acetonitrile and a picoline in a ratio of 1.5:1 to 1:1.5.

3. The method of claim 1 wherein said solvent mixture is acetonitrile and a picoline in a ratio of 1.5:1 to 1:1.5.

4. The method of claim 3, wherein said picoline is 3-picoline.

5. The method of claim 4 wherein said ratio is 1:1.

6. The method of claim 1 wherein said arylacetyl disulfide is phenylacetyl disulfide.

7. The method of claim 1 wherein said phosphite moiety is a phosphoramidite group that is bonded to a nucleoside.

8. The method of claim 1 wherein said phosphite diester intermediate is a phosphite linked dinucleotide.

9. The method of claim 8 wherein said dinucleotide is formed by reaction of a phosphoramidite group.

10. The method of claim 1 wherein said phosphite moiety is attached to an oligonucleotide.

11. The method of claim 10 wherein said phosphite moiety is a phosphoramidite group.

12. A method for the preparing an oligonucleotide wherein at least one of the internucleoside linkages is a phosphorothioate internucleoside linkage prepared according to the method of claim 1 and wherein said oligonucleotide comprises from about 8 to about 30 nucleotides.

13. The method of claim 12 wherein said oligonucleotide comprises about 20 nucleotides.

* * * * *